United States Patent
Koverech

(10) Patent No.: US 8,013,016 B2
(45) Date of Patent: Sep. 6, 2011

(54) USE OF ACETYL L-CARNITINE FOR THE TREATMENT OF FIBROMYALGIC SYNDROME

(75) Inventor: Aleardo Koverech, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 498 days.

(21) Appl. No.: 11/719,447

(22) PCT Filed: Nov. 10, 2005

(86) PCT No.: PCT/EP2005/012054
§ 371 (c)(1),
(2), (4) Date: Oct. 11, 2007

(87) PCT Pub. No.: WO2006/063639
PCT Pub. Date: Jun. 22, 2006

(65) Prior Publication Data
US 2009/0076146 A1    Mar. 19, 2009

(30) Foreign Application Priority Data
Dec. 13, 2004 (IT) .............................. RM2004A0606

(51) Int. Cl.
*A61K 31/225* (2006.01)
*A61P 29/00* (2006.01)
(52) U.S. Cl. ..................................................... 514/547

(58) Field of Classification Search .................... None
See application file for complete search history.

(56) References Cited

U.S. PATENT DOCUMENTS

| 4,464,393 | A | * | 8/1984 | Cavazza ........................ 514/556 |
| 5,576,348 | A | * | 11/1996 | Kuratsune et al. ............. 514/547 |
| 5,935,949 | A | * | 8/1999 | White ............................. 514/178 |
| 6,025,368 | A | * | 2/2000 | Mascarenhas et al. ........ 514/310 |
| 2004/0044018 | A1 | * | 3/2004 | Fisher et al. .................. 514/278 |
| 2004/0198837 | A1 | | 10/2004 | Mendel et al. |

FOREIGN PATENT DOCUMENTS
WO    WO 02/096409    12/2002

OTHER PUBLICATIONS

Rao et al. Best Practice & Research Clinical Rheumatology, 17(4): 611-627, 2003.*
Spaeth et al., Poster #479, ACR poster Section B, Soft Tissue & Regional Musculoskeletal Disorders, Nov. 14, 1999.*
Onofrj M., et al., L-Acetyl Carnitine as a New Therapeutic . . . , Int. J. Clin. Pharm. Res. vol. 15, pp. 9-15, 1995.

* cited by examiner

Primary Examiner — Jeffrey S. Lundgren
Assistant Examiner — Bong-Sook Baek
(74) Attorney, Agent, or Firm — Lucas & Mercanti, LLP

(57) ABSTRACT

The use of acetyl L-carnitine or one of its pharmaceutically acceptable salts is described for the preparation of a medicament and/or dietetic product for the treatment of fibromyalgic syndrome.

3 Claims, No Drawings

USE OF ACETYL L-CARNITINE FOR THE TREATMENT OF FIBROMYALGIC SYNDROME

The present invention relates to the use of acetyl L-carnitine for the preparation of a medicament for the treatment of fibromyalgic syndrome.

Fibromyalgic syndrome or fibromyalgia is a chronic pain syndrome characterised by diffuse arthromyalgias accompanied to varying extents by sleep disorders, muscle-tension headache, irritable bowel syndrome, and asthenia.

The symptoms sometimes present in isolation and sometimes in association with other rheumatic diseases or with endocrine and metabolic diseases, particularly dysthyroidism (Arthritis Rheum 1983; 26: 817-824; Seminar Arthritis Rheum 1981; 11:151-71).

The condition is distinctly more prevalent in subjects of female gender and is more frequent in patients aged from 25 to 55 years.

The cause of fibromyalgia is still unknown and various pathogenetic mechanisms are currently postulated, such as psychic disturbances, alteration of normal sleep activity and of the pain perception threshold, and functional disorders affecting skeletal muscle with the presence of morphological alterations of the muscle fibre cells (Scand. J. Rheumatol. 1986; 15: 1-6) or various metabolic deficits (Bull Rheum Dis 1978; 26: 928-931; J. Rheumatol 1992; 19:90-94).

The diagnosis of fibromyalgia is obtained on a purely clinical basis (medical history and physical examination) since laboratory tests (haematology and blood chemistry) and instrumental investigations (radiology, electrophysiology) yield no diagnostically useful indications in this clinical picture.

Medical history and physical examination are therefore decisive for the purposes of identifying this syndrome. The location of the pain, described as experienced "all over", the abundance and colourfulness of the terms the patient uses to describe it, the plentiful array of associated symptoms, including headache, irritable bowel syndrome, and sleep disorders, and the history of numerous examinations by specialists and instrumental investigations may suggest the diagnosis of a clinical picture indicative of a "fibrositic situation". The symptoms are generally experienced mainly in the morning, deteriorate with fatigue, physical activity, stress and changes in the weather, but improve with massage and periods of rest and recreation. At the physical examination an excessive muscular tension is noted, even to the extent of an actual contracture affecting typical muscular districts such as the sternocleidomastoid, trapezius and paravertebral muscles where tender points need to be sought (Br Med J 1994; 309: 696-9).

Essential for the diagnosis of fibromyalgia is the demonstration of deep tender points with areas of increased soft tissue consistency (Arthritis Rheum 1990; 33(2): 160-172). Tender points differ from trigger points, in that they do not cause referred and irradiated pain, but prove tender only in the site stimulated. The simplest technique for detecting tender points is simple digital pressure (approximately 4 kg with the digital pulp) or by pinching the skin at points corresponding to definite joints and tendon insertions. Pressure on these points is accompanied by an exaggerated reaction of withdrawal from the examiner, jump sign, and neurovegetative phenomena such as dermographia, horripilation, and cold sweats. The tender points most commonly used for diagnostic purposes are nine in number (bilaterally), and to exemplify the diagnostic and classificatory approach criteria have been defined for locating and evaluating the tender points present in the patient (Arthritis Rheum 1990; 33(2): 160-172).

Previous therapeutic uses of acetyl L-carnitine are already known.

U.S. Pat. No. 4,751,242 describes the use of acetyl L-carnitine for the treatment of peripheral neuropathies.

U.S. Pat. No. 4,362,719 describes the use of L-carnitine and acyl L-carnitines for the treatment of juvenile onset diabetes mellitus.

U.S. Pat. No. 5,192,805 relates to the use of acetyl L-carnitine in the therapeutic treatment of coma.

U.S. Pat. No. 6,037,3721128 relates to the use of acetyl L-carnitine, isovaleryl L-carnitine and propionyl L-carnitine to increase IGF-1 levels, for the treatment of lateral amyotrophic sclerosis, neuropathies of the optic and olfactory nerves, trigeminal nerve neuralgia and other pathologies.

U.S. Pat. No. 6,037,372 relates to the use of an L-carnitine alkanoyl, including acetyl L-carnitine, for the treatment of pathologies mediated by glutamate such as epilepsy, schizophrenia, chronic fatigue syndromes lateral amyotrophic sclerosis and others.

Acetyl L-carnitine, a commercially available product, can be prepared with the process described by R. Krinmberg, and W. Wittandt, in Biochem. Z. 251, 229 (1932).

Fibromyalgia, despite being a clinical condition with a benign course, is difficult to treat (Rheum Dis Clin N Am 1989; 15:61-71).

The patients often use anti-inflammatory drugs which, in addition to having no pharmacological rationale in this condition, are ineffective.

Muscle relaxants and antidepressant drugs have also been used for the treatment of this disease, but only improve the quality of sleep (Arthritis Rheum 1986; 29: 1371-7; Arthritis Rheum 1994, 37: 3240).

Good results, albeit short-lasting, have also been obtained by means of local infiltration of the tender points with anaesthetics.

There is therefore a strongly perceived need for the availability of new drugs useful for the treatment of fibromyalgia which are more effective and do not present the drawbacks of the above-mentioned known drugs.

It has now been found that acetyl L-carnitine or one of its pharmaceutically acceptable salts is a useful compound for the treatment of fibromyalgia.

What is meant by pharmaceutically acceptable salt of acetyl L-carnitine is any salt prepared by addition of an acid to acetyl L-carnitine inner salt, and which does not give rise to unwanted toxic or side effects. The formation of salts by addition of an acid is well known in pharmaceutical technology.

Non-limitative examples of such salts are chloride, bromide, orotate, aspartate, acid aspartate, citrate, acid citrate, magnesium citrate, phosphate, acid phosphate, fumarate, acid fumarate, magnesium fumarate, glycerophosphate, lactate, maleate and acid maleate, mucate, oxalate, acid oxalate, pamoate, acid pamoate, sulphate, acid sulphate, glucose phosphate, tartrate, acid tartrate, magnesium tartrate, 2-amino ethanesulphonate, magnesium 2-amino ethanesulphonate, methane-sulphonate, choline tartrate, trichloroacetate, and trifluoroacetate.

The subject of the present invention is therefore the use of acetyl L-carnitine or of one of its pharmaceutically acceptable salts for the preparation of a medicament and/or dietetic product for the treatment of fibromyalgia.

The acetyl L-carnitine can be in any form suitable for oral or parenteral administration. It can be administered in the form of a unit dose or in divided doses, in amounts ranging from 40 mg to 4 g/day.

The preferred dose according to the present invention is 1.5 g per day, administered at the start of treatment and for the first 2 weeks at the dose of 500 mg intramuscularly (i.m.) and 500 mg (twice daily) orally (os), the treatment thereafter being continued with oral doses of 500 mg three times daily.

The daily dose will depend, according to the judgement of the primary care physician, on the patient's weight, age and condition. Larger doses of acetyl L-carnitine can be administered thanks to the extremely low toxicity of said active ingredient.

The following examples illustrate the invention.

A multicentre, randomized, placebo-controlled, double-blind clinical trial was conducted, the aim of which was to evaluate the efficacy of acetyl L-carnitine in patients with fibromyalgic syndrome.

For the evaluation of the efficacy of the compound according to the present invention evoked pain was monitored (as measured with the "Pressure Threshold Meter" algometer) in the osteoarticular regions indicated by "The American College of Rheumatology" (ACR) as being "tender points" characteristic of fibromyalgia syndrome. [WOLFE F, SMYTHE H A, YUNUS M B, et al. The American College of Rheumatology Criteria for the classification of fibromyalgia: report of the multicenter criteria committee; Arthritis Rheum 1990; 33(2): 160-172].

Also monitored were additional secondary parameters which will be discussed later.

The evaluation of the tolerability of the treatment was done by means of routine haematological and blood-chemistry tests and by recording adverse events.

The patients included in the trial were patients of either gender aged from 25 to 65 years, who matched up to the above-mentioned American College of Rheumatology diagnostic criteria for fibromyalgia syndrome.

The diagnostic criteria for fibromyalgic syndrome had to be confirmed by the presence of all four of the following conditions:
  bilateral diffuse pain in the axial skeleton;
  bilateral diffuse pain in the upper limbs;
  bilateral diffuse pain in the lower limbs;
  pain located in 11 or more of the 18 anatomical regions listed in the map of tender points (ACR tender points) evoked with a standardised pressure manoeuvre.

Patients with any one of the following conditions were not recruited into the trial:
  presence of infections or inflammatory processes affecting the osteoarticular or tegumental apparatus;
  history or presence of clinically important osteoarticular disease capable of confounding the evaluation of the study treatments (e.g. history of trauma);
  previous orthopaedic surgery, spondyloarthrosis, connectivitis etc.;
  clinical or laboratory evidence of dysthyroidism;
  presence of systemic diseases (diabetes, kidney, cardiovascular and respiratory disease, psychiatric illness) or major pathological conditions capable of interfering with the evaluation of the study treatments;
  continuous use of anti-inflammatory steroids during the last 3 months prior to the trial;
  recent initiation of oestrogen-progestogen hormone replacement therapy (<1 year);
  therapy with antidepressant drugs during the last 6 months prior to the trial;
  therapy with non-steroidal anti-inflammatory drugs during the last 3 days prior to the trial;
  therapy with analgesic drugs during the last 7 days prior to the trial;
  participation in a clinical trial during the previous 6 months;
  pregnant women, breastfeeding women, or women of childbearing age not adopting an adequate contraceptive method.

Acetyl L-carnitine was administered for a period of 10 consecutive weeks at a dose of 1,500 mg/day.

During the first two weeks it was administered at the dose of 500 mg by the intramuscular route (i.m.) and 500 mg (twice daily) by the oral route (os).

Over the following eight weeks acetyl L-carnitine was administered orally at doses of 500 mg three times daily.

The results obtained are given in Table 1 here below.

TABLE 1

| | Mean variation compared to baseline | | |
| Visit | Placebo (N = 47) | Acetyl L-carnitine (N = 42) | P (Student's t-test) |
| --- | --- | --- | --- |
| 2 weeks | 0.16 (0.39) | 0.24 (0.64) | — |
| 6 weeks | 0.45 (0.57) | 0.55 (0.64) | — |
| 10 weeks | 0.34 (0.66) | 0.71 (0.71) | <0.05 |

The results obtained, presented in Table 1, show that at the end of therapy the patients treated with the compound according to the present invention had a statistically significant improvement in pain evoked in the osteoarticular regions (the above-mentioned ACR regions) indicated as tender points characterised by fibromyalgic syndrome as compared to the control group.

In addition, at the end of the treatment period the patients treated with the compound according to the invention presented statistically significant improvements (assessed with visual analogue scales) in secondary clinical parameters relating to general well-being, mental health, and physical health in general (P<0.05).

Pomezia,

The invention claimed is:

1. A method of treating fibromyalgia, consisting of administering an effective amount of a medicament consisting of acetyl L-carnitine or one of its pharmaceutically acceptable salts and pharmaceutically acceptable carriers and/or excipients to a patient in need thereof, wherein said effective amount is 1.5 g per day, wherein for the first two weeks of treatment administration of said effective amount consists of administering daily 500 mg intramuscularly once a day and 500 mg orally twice a day.

2. The method according to claim 1, in which the pharmaceutically acceptable salt of acetyl L-carnitine is selected from the group consisting of chloride, bromide, orotate, aspartate, acid aspartate, citrate, acid citrate, magnesium citrate, phosphate, acid phosphate, fumarate, acid fumarate, magnesium fumarate, glycerophosphate, lactate, maleate and acid maleate, mucate, oxalate, acid oxalate, pamoate, acid pamoate, sulphate, acid sulphate, glucose phosphate, tartrate, acid tartrate, magnesium tartrate, 2-amino ethansulphonate, magnesium 2-amino ethansulphonate, methansulphonate, choline tartrate, trichloroacetate, and trifluoroacetate.

3. The method according to claim 1, wherein after the first two weeks period said treatment consists of administering 500 mg orally three times daily.

* * * * *